United States Patent [19]

Molteni et al.

[11] 4,313,943
[45] Feb. 2, 1982

[54] 7-CHLORO-2,3-DIHYDRO-5-PHENYL-1-PROPARGYL-1H-1,4-BENZODIAZEPINE-2-ONE, AND A PHARMACEUTICAL COMPOSITION THEREOF

[76] Inventors: Luigi Molteni, Corso Porta Romana, 69; Franco Tenconi, Via Palestrina 20; Renato Tagliabue, Via Veneto 3, all of Milan, Italy

[21] Appl. No.: 715,690

[22] Filed: Aug. 19, 1976

Related U.S. Application Data

[63] Continuation-in-part of Ser. No. 383,993, Jul. 30, 1973, abandoned.

[30] Foreign Application Priority Data

Aug. 9, 1972 [IT] Italy .................. 28048 A/72

[51] Int. Cl.³ .................... C07D 243/24; A61K 31/55
[52] U.S. Cl. ............................. 424/244; 260/239.3 D
[58] Field of Search ................. 260/293.3 D; 424/244

[56] References Cited

U.S. PATENT DOCUMENTS

3,371,085 2/1968 Reeder et al. .............. 260/239.3 D
3,842,094 10/1974 Podesva et al. ............. 260/239.3 D

FOREIGN PATENT DOCUMENTS

2339790 2/1974 Fed. Rep. of Germany.. 260/239.3 D
2195447 3/1974 France ..................... 260/239.3 D

OTHER PUBLICATIONS

Sternbach et al., "Some Aspects of Structure–Activity Relationship in Psychotropic Agents of the 1,4-Benzodiazepine Series, *CSIR* New Delhi, India, (1966).

*Primary Examiner*—Robert T. Bond
*Attorney, Agent, or Firm*—Hill, Van Santen, Steadman, Chiara & Simpson

[57] ABSTRACT

The invention relates to 1-propargyl-5-(halo) phenyl-1,4-benzodiazepines, and particularly to 7-chloro-2,3-dihydro-5-phenyl-1-propargyl-1H-1,4-benzodiazepine-2-one endowed with psycho-sedative, low myorelaxant, high anxiolytic, anticonvulsant and hypnotic properties.

2 Claims, No Drawings

7-CHLORO-2,3-DIHYDRO-5-PHENYL-1-PROPARGYL-1H-1,4-BENZODIAZEPINE-2-ONE, AND A PHARMACEUTICAL COMPOSITION THEREOF

This is a continuation-in-part of our earlier U.S. Ser. No. 383,993, filed July 30, 1973 now abandoned, which is incorporated herein by reference.

This invention relates to a group of novel, pharmaceutically useful benzodiazepine derivatives.

The compounds of the invention are 1-propargyl-1,4-benzodiazepines of formula:

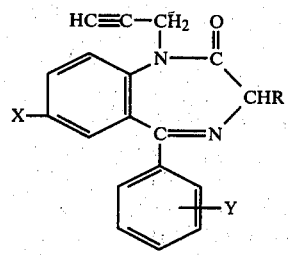

wherein:
R represents a hydrogen atom or a hydroxyl group;
X represents a chlorine atom, a bromine atom, a methyl group, a trifluoromethyl group or a nitro group; and
Y represents a hydrogen atom, a chlorine atom or a fluorine atom; and pharmaceutically acceptable acid addition salts thereof.

Specific examples of the compounds of the invention are:
7-chloro-2,3-dihydro-5-phenyl-1-propargyl-1H-1,4-benzodiazepin-2-one;
7-nitro-2,3-dihydro-5-phenyl-1-propargyl-1H-1,4-benzodiazepin-2-one;
and pharmaceutically acceptable acid addition salts thereof.

The compounds of the invention can be prepared by reacting a propargyl halide with a metallic derivative of a benzodiazepine of formula:

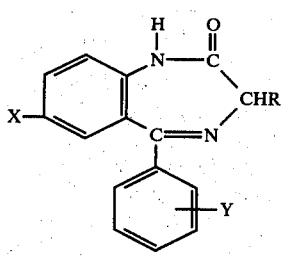

(wherein R, X and Y have the meanings already given) and, if appropriate, salifying the product of the reaction.

The propargyl halide used in the reaction can be propargyl chloride, bromide or iodide, most preferably the bromide. The reaction medium is suitably dimethylformamide, a mixture of dimethylformamide and toluene, or absolute ethanol; and the reaction is preferably performed at a temperature from 0° C. to 50° C. The product of the reaction can be purified by conventional techniques, for example, by column chromatography.

The metallic derivative of the benzodiazepine of formula (II) can be prepared by reacting this benzodiazepine with a metal hydride or metal alkoxide, generally an alkali metal hydride or alkoxide such as sodium hydride or sodium methoxide. This reaction is performed at a temperature not higher than 15° C., preferably from 0° to 10° C., with stirring, and typically takes about 2 hours. The reaction with the propargyl halide can then be carried out in situ, without isolating the metallic derivative of the benzodiazepine.

Pharmaceutically acceptable acid addition salts of the compounds of formula (I) can be prepared in the conventional manner, for example, by acidifying a chloroform solution of the free base with an acid such as hydrochloric or sulphuric acid in absolute ethanol, and precipitating the salt (e.g. by the addition of ether). The salt thus obtained can be purified, for example, by recrystallization from absolute ethanol.

It has been found that the compounds of the invention are endowed with valuable pharmacological and therapeutic properties. Specifically, the compounds of the invention combine potent and long-lasting psychosedative, myorelaxant, anti-convulsant and hypnotic activity with low toxicity. Their properties compare very favorably with those of commonly used benzodiazepines, for example, diazepam.

A preferred compound of the invention is: 7-chloro-2,3-dihydro-5-phenyl-1-propargyl-1H-1,4-benzodiazepin-2-one, which, in addition to the above recited properties, exhibits relatively high anxiolytic and relatively low myorelaxant properties.

Accordingly, the invention also provides a pharmaceutical composition, comprising a compound of formula (I), or a pharmaceutically acceptable acid addition salt thereof, and a pharmaceutical carrier or diluent. The pharmaceutical composition of the invention may be formulated in the conventional manner, with solid or liquid carriers or diluents, and with appropriate pharmaceutical adjuvants. Suitable formulations include tablets, capsules, powders, suspensions and syrups for oral administration, and injectible solutions and suspensions for parenteral administration.

The pharmacological properties of the compounds of the invention are illustrated by the following tests, wherein "Test Compound 1" is the preferred embodiment of the invention, i.e., 7-chloro-2,3-dihydro-5-phenyl-1-propargyl-1H-1,4-benzodiazepin-2-one; and "Test Compound 2" is 7-nitro-2,3-dihydro-5-phenyl-1-propargyl-1H-1,4-benzodiazepin-2-one.

Motor Coordination in the Rat

(Rota-rod method)

The method of Dunham and Miya was used, which consists in placing the test animal on a rod rotating at 14 r.p.m., and recording the percentage of animals which fall off within 2 minutes. The test compound 1 was administered orally to the animals, in the various doses shown in Table 1, as a suspension in 1% sodium carboxymethyl cellulose solution. The animals were then tested 30 minutes and 60 minutes after the administration of the test compound. The results obtained are shown in Table 1.

TABLE 1

| Test Compound | Dose (mg/kg) | Percentage of animals falling within 2 minutes | |
|---|---|---|---|
| | | 30 minutes after administration | 60 minutes after administration |
| 1 | 3 | 0 | 0 |
| 1 | 6 | 50 | 17 |

TABLE 1-continued

| Test Compound | Dose (mg/kg) | Percentage of animals falling within 2 minutes | |
|---|---|---|---|
| | | 30 minutes after administration | 60 minutes after administration |
| 1 | 12 | 100 | 50 |

Acute Toxicity in the Mouse and Rat

The test compounds shown in Table 2 were administered orally to male mice and rats in the form of a suspension in a 1% solution of sodium carboxymethyl cellulose. The $LD_{50}$ (lethal dose 50%) was calculated by the method of Litchfield and Wilcoxon. The results obtained are shown in Table 2.

TABLE 2

| Test Compound | Test Animal | $LD_{50}$(Mg/kg) |
|---|---|---|
| 1 | Mouse | 1,302 |
| 1 | Rat | 6,489 |
| 2 | Mouse | 1,875 |
| 2 | Rat | 876 |

Anti-Convulsant Activity in the Mouse

The inhibition of convulsions induced by 1,5-pentamethylenetetrazole was tested by the Clen method. The test compounds were administered orally to the mice, in the doses shown in Table 3, in the form of suspensions in 1% sodium carboxymethyl cellulose solution, and 30 minutes later the test animals were injected subcutaneously with 150 m/kg of 1,5-pentamethylenetetrazole. The number of mice protected from lethal extensorial tonic spasms, per group of 10 test animals, was recorded. The results obtained are shown in Table 3.

TABLE 3

| Test Compound | Dose (mg/kg) | No. of Animals Protected |
|---|---|---|
| 1 | 0.5 | 0/10 |
| 1 | 1.0 | 5/10 |
| 1 | 2.0 | 9/10 |
| 2 | 0.12 | 1/10 |
| 2 | 0.25 | 4/10 |
| 2 | 0.50 | 9/10 |

Potentiation of Narcosis in the Mouse

The Winter method was used, in which a state of narcosis is induced by the intraperitoneal administration of 80 mg/kg of hexobarbitone sodium, and is assessed by the loss of the righting reflex in the test animal. 60 minutes after the hexobarbitone administration, the test compounds were administered orally to the animals, in doses shown in Table 4, as suspensions in 1% sodium carboxymethyl cellulose solution; and the prolongation of narcosis in the animals thus treated was observed, by comparison with controls which received only the hexobarbitone administration. The results obtained are shown in Table 4.

TABLE 4

| Test Compound | Dose (mg/kg) | Duration of narcosis (minutes) |
|---|---|---|
| None (control) | — | 33.3 |
| 1 | 1.0 | 70.7 |
| 1 | 2.0 | 111.3 |
| 2 | 0.5 | 53.4 |
| 2 | 1.0 | 94.5 |
| 2 | 2.0 | 195.1 |

Myorelaxant Activity in the Mouse

This was determined by the traction test of Joulon Courvoisier, following Boissier and Simon, in which the mouse is suspended by its front paws to a horizontal metal wire, and the animal's capacity to get up with its hind paws is observed. The test compounds were administered orally to the animals, in the doses shown in Table 5, as suspensions in 1% sodium carboxymethyl cellulose solution; and the animals were tested 30 minutes and 180 minutes after administration. The test animals were deemed to be myorelaxant if unable to get up within 5 seconds. The results obtained are shown in Table 5.

TABLE 5

| Test Compound | Dose (mg/kg) | Percentage of myorelaxant animals after | |
|---|---|---|---|
| | | 30 minutes | 180 minutes |
| 1 | 1.5 | 20 | 15 |
| 1 | 3.0 | 60 | 55 |
| 1 | 6.0 | 80 | 70 |
| 2 | 1.0 | 10 | — |
| 2 | 2.0 | 20 | — |
| 2 | 4.0 | 40 | — |
| 2 | 8.0 | 60 | — |

Additional properties of the compounds of the invention are further illustrated by the following tests, where "Test Compound 1" again is the preferred embodiment of the invention, i.e., 7-chloro-2,3-dihydro-5-phenyl-1-propargyl-1H-1,4-benzodiazepin-2-one; "Test Compound 3" is diazepin, i.e., 7-chloro-1,3-dihydro-1-methyl-5-phenyl-2H-1,4-benzodiazepin-2-one; and "Test Compound 4" is 7-chloro-2,3-dihydro-5-(2-chlorophenyl)-1-propargyl-1,H-1,4-benzodiazepine-2-one).

Comparative Tranquilizing Effects

The method utilized was the 4 plates test of J. R. Boissier, et al (European J. of Pharm. 1968, Vol. 4, pages 145-151). The dosages and results obtained are summarized in Table 6. As can be seen from this data, compound 1 exerts a more effective anxiolytic effect than compound 4 and does not produce changes in motor activity or in equilibrium (rotarod test) as caused by compound 4 at the same dosage level. Duration of effect of compounds 1 and 4 are comparable.

TABLE 6

| | Four Plates Test | Reduction in Motor Activity Between 60 and 90 Minutes | | | | Rotarod Test % of Animals With Unchanged Equilibrium | | | |
|---|---|---|---|---|---|---|---|---|---|
| | | Composition 1 | | Composition 4 | | Composition 1 | | Composition 4 | |
| | | 1 mg/kg | 3 mg/kg | 1 mg/kg | 3 mg/kg | 1 mg/kg | 3 mg/kg | 1 mg/kg | 3 mg/kg |
| $ED_{50}$ mg/kg[1] 60 min. after administration[2] | Comp. 1 = 1.75 (1.10–2.78 mg/kg) Comp. 4 | +19% | −20% | −69% | −82% | 41.7% | 58.3% | 50.0% | 8.3% |

TABLE 6-continued

| Four Plates | Reduction in Motor Activity Between 60 and 90 Minutes | | | | Rotarod Test % of Animals With Unchanged Equilibrium | | | |
|---|---|---|---|---|---|---|---|---|
| | Composition 1 | | Composition 4 | | Composition 1 | | Composition 4 | |
| Test | .1 mg/kg | 3 mg/kg | .1 mg/kg | 3 mg/kg | 1 mg/kg | 3 mg/kg | 1 mg/kg | 3 mg/kg |
| 5.5 mg/kg[3] | NS | NS | 0.002 | 0.002 | | | | |

1. Doses given were between 0.5 and 4 mg/kg.
2. $ED_{50}$ and confidence limits for P = 0.05
3. Over 3 mg/kg caused motor activity to be so reduced that 4 plates test cannot be used.

Effect on Muscular Relaxation in Mice

The method utilized was the procedure described by Randall (1961) using a 30° inclined screen. The dosages and results obtained are shown in Table 7. These results show that compound 1 is about 5.6 times less relaxant than compound 4 and about 1.5 times less relaxant than compound 3.

TABLE 7

| Test Compound | mg/kg/os | % Relaxed Animals | $ED_{50}$ and C.L. | $X^2$ Parallelism | Potency and C.L. Against Comp. 1 |
|---|---|---|---|---|---|
| CMC 1% | — | 0 | | | |
| 1 | 5 | 10 | | | |
| 1 | 10 | 20 | 21.50 | | |
| 1 | 20 | 50 | (11.00–42.03) | 2.03 | 5.60 |
| 1 | 40 | 70 | | | (1.67–18.80) |
| 4 | 2 | 40 | 3.93 | | |
| 4 | 8 | 60 | (1.09–14.16) | | |
| 4 | 32 | 80 | 14.14 | | |
| 3 | 10 | 20 | (6.16–32.42) | — | — |

Effect on Emotional Conditioning Response in Rats

The method utilized that was published by Brady (1956) using a Skinner Box and a combination of a sound, a light and an electrical shock to produce anxiety in the test animals.

The more an animal is anxious, the less important is the score. When a test compound is a powerful anxiolytic, the value of the score is proportional to the dosage. The results obtained and dosages are shown in Tables 8A and 8B. As can be seen, Composition 1 is twice as effective in reducing anxiety as Composition 4.

TABLE 8A

| Test Compound | mg/kg/os | Number of Responses | | |
|---|---|---|---|---|
| | | Before - CER | CER | After - CER |
| 1 | 0 | 54.00 ± 15.30 | 7.33 ± 3.96 | 50.63 ± 17.33 |
| 1 | 1.25 | 94.67 ± 13.86 | 27.50 ± 11.32 | 77.83 ± 20.41 |
| 1 | 0 | 77.30 ± 17.03 | 8.30 ± 1.34 | 62.20 ± 14.78 |
| 1 | 2.5 | 142.10 ± 20.03 | 62.10 ± 9.59 | 112.30 ± 17.56 |
| 1 | 0 | 66.00 ± 13.87 | 5.25 ± 1.73 | 57.00 ± 14.74 |
| 1 | 5 | 127.13 ± 20.89 | 63.50 ± 14.96 | 128.75 ± 17.13 |
| 4 | 0 | 88.43 ± 17.87 | 7.35 ± 2.32 | 70.85 ± 13.77 |
| 4 | 1.25 | 81.28 ± 16.17 | 26.25 ± 4.57 | 86.43 ± 22.13 |
| 4 | 0 | 84.75 ± 17.33 | 7.00 ± 1.07 | 73.25 ± 9.52 |
| 4 | 2.5 | 66.75 ± 11.80 | 31.12 ± 6.54 | 79.75 ± 15.24 |

TABLE 8A-continued

| Test Compound | mg/kg/os | Number of Responses | | |
|---|---|---|---|---|
| | | Before - CER | CER | After - CER |
| 4 | 0 | 86.50 ± 16.54 | 6.88 ± 1.65 | 65.00 ± 10.88 |
| 4 | 5 | 65.00 ± 14.89 | 38.37 ± 8.76 | 79.00 ± 20.03 |

TABLE 8B

Coefficients and potency of linear regressions of conditional responses on the log doses of the test compounds

| Test Compound | Linear Regression Coefficients | | F Parallelism | Potency and C. L. |
|---|---|---|---|---|
| | a ± Sa | b ± Sb | | |
| 1 | 3.93 ± 1.94 | 16.93 ± 8.48 | <1 | 0.80 / 2.03 \ 5.10 |
| 4 | 1.97 ± 1.38 | 11.27 ± 5.70 | | |

The same CER (conditioned emotional response) test was conducted between Compounds 1 and 3 and it was noted that Compound 1 is about twice as active as Compound 3 in antagonizing the CER of test animals.

Comparative Tranquilizing Effect on Motor Coordination in Rats

The method utilized was that described by Dunham and Miya (1957) using a rotarod. The test animals received the compounds orally. The results obtained and dosages used are shown in Table 9. As can be seen from these results, animals must receive about five times more of Compound 1 to present the same motor uncoordination as present after Compound 3 or 4 administration.

TABLE 9

| Test Compound | mg/kg/os | % Uncoordinated Animals | $ED_{50}$ and C.L. | $X^2$ Parallelism | Potency and C.L. Against Comp. 1 |
|---|---|---|---|---|---|
| CMC 1% | — | 0 | | | |
| 1 | 48 | 25 | | | |
| 1 | 68 | 50 | 67.9 | | 4.58 |
| 1 | 96 | 75 | (47.6–96.9) | 0.005 | (3.09, 6.79) |
| 4 | 12 | 37.5 | 14.9 | | |
| 4 | 17 | 50 | (10.7–20.7) | | |
| 4 | 24 | 87.5 | | | |
| 3 | 68 | 50 | 14.20 | | |

TABLE 9-continued

| Test Compound | mg/kg/os | % Uncoordi- nated Animals | $ED_{50}$ and C.L. | $X^2$ Parallelism | Potency and C.L. Against Comp. 1 |
|---|---|---|---|---|---|
| | | | (8.38–24.01) | | |

Comparative Effect On Convulsions Induced By Pentamethylenetetrazol in Rats

The method utilized was according to the method published by Everett and Richards (1944) and Banziger (1965). The pentamethylenetetrazol was given subcutaneously (125 mg/kg) and the test compounds were given orally suspended in a 1% carboxymethyl cellulose solution.

The dosages and results obtained are shown in Tables 10A and 10B. As can readily be seen from these results, compounds 1 and 4 exert a comparable effect, the $ED_{50}$ being respectively 10:6 (7.3–16.4) mg/kg and 8.5 (6.6–11.1) mg/kg. However, the cinetic of effects, i.e., the effect of each compound as a function of time shows that compound 1 protects against pentamethylenetetrazol for longer periods of time than compounds 3 or 4.

TABLE 10A

| Test Compound | mg/kg/os | % Protected Animals | $ED_{50}$ and C.L. |
|---|---|---|---|
| CMC 1% | — | 0 | |
| 1 | 5 | 10 | |
| 1 | 10 | 50 | 10.6 |
| 1 | 20 | 80 | (7.3–16.4) |
| 4 | 6 | 20 | |
| 4 | 8.5 | 60 | 8.5 |
| | | | (6.6–11.1) |
| 4 | 12 | 70 | |
| 3 | — | — | 7.8 |
| | | | (16.3–9.8) |

TABLE 10B

| | % Protected Animals | | |
|---|---|---|---|
| Time in Min. | Comp. 1 | Comp. 4 | Comp. 3 |
| 90 | 48 | 37 | 20 |
| 120 | 46 | 18 | 10 |
| 180 | 37 | 0 | 0 |
| 240 | 10 | 0 | 0 |

Acute Toxicity and Hypnotic Activity Comparison

Toxicity in test animals to the test compounds in terms of $LD_{50}$ after oral and intraperitoneal administration was determined according to the procedure of Litchfield and Wilcoxan (1949) and the hypnotic effect on test animals was determined in accordance with the method of Janssen (1959).

The results obtained are shown in Table 11 and it can be seen that Compound 1 has a lower oral toxicity and a lower hypnotic activity than Compounds 3 or 4.

TABLE 11

| Test Compound | $LD_{50}$ mg/kg | $ED_{50}$ mg/kg |
|---|---|---|
| 1 | 5819 | 857.2 |
| | (4854–6975) | (561.1–1301.2) |
| 3 | 2075 | 242.5 |
| | (1760–2445) | (145.1–405.3) |
| 4 | >5000 | |

Effect on Behavior

The aggressive behavior of test animals was elicited by a conventional foot shock procedure after administration of Compounds 1 and 4. On a weight basis, both Compounds 1 and 4 exerted a similar effect and the oral $ED_{50}$ was, respectively, 3.3 and 2.7 mg/kg.

Spontaneous mobility in test animals was determined by the Svenson and Thieme procedure as published in Psychopharmacologia, Vol. 14, 1969, pages 157 et seq. On the basis of the results obtained, it was noted that Compound 1 was approximately three times less active than Compound 4 in depressing spontaneous mobility. The oral $ED_{50}$ was, respectively, 76.6 and 20.1 mg/kg.

Conditioned avoidance response by trained animals in a conventional shuttle box procedure was determined after oral administration of Compounds 1 and 4. The results are tabulated below in Table 12 and as can be seen, Compound 1 is less active than Compound 2 in reducing the number of conditioned avoidance responses.

TABLE 12

| Test Compound | Dose mg/kg | Number of Conditioned Avoidance Responses | % Decrease |
|---|---|---|---|
| CMC 1% | — | 16.7 ± 0.3 | |
| 1 | 5 | 14.5 ± 0.7 | −12 |
| 1 | 10 | 13.4 ± 0.7 | −19 |
| 1 | 20 | 13.7 ± 0.9 | −17 |
| 1 | 40 | 9.3 ± 1.5 | −44 |
| 4 | 5 | 9.2 ± 1.4 | −44 |
| 4 | 10 | 2.5 ± 1.5 | −85 |

Conditioned emotional response (CER) in test animals was conventionally determined by a tone paired with a foot shock which was presented to hungry animals trained to press a lever for intermittent food reinforcement. After a few such pairings, the presence of the tone alone was sufficient to disrupt the lever pressing behavior. CER is considered a model of behavior anxiety in animals. The results obtained indicated that Compound 1 is about twice as active as Compound 4 in antagonizing the tone-induced disruption. Thus, a 1.25 mg/kg os of compounds 1 and 4 respectively produced about a 350 and 630% increase in CER while a 5 mg/kg os of compounds 1 and 4 respectively produced about 920 and 1600% increase.

Comparative Neurophysiological Effects

This demonstration, with a group of unanesthetized animals, was designed to determine the target points of test compounds 1 and 4 in the central nervous system and in so doing to differentiate through the respective compound activity, the two chemically similar compounds.

For this purpose, the demonstration included the following elements:

A. A timed study of modifications induced by the compounds in cortical electrogenesis in the nonanesthetized animal.

B. A study of the more specific modifications in electric activity recorded from various subcortical centers, such as the caudate nucleus, hippocampus, the rhinencephalic amygdaloid complex, the median and lateral thalamus and the mesencephalic and hypothalamic reticular formations.

Observations of any depressive action which might appear in the centers were maintained while the animals were in a state of vigilance. This was achieved by high frequency stimulation (200 c/sec.) of the mesencephalic reticular formation (basal vigilance, the median thalamus (focalized vigilance) and the posterior hypothalamus (effective vigilance).

C. Lastly, the study sought to determine the existence of a direct effect in the rhinencephalic region, through variations in morphology and the duration of after-discharges following electrical stimulation of the dorsal hippocampus and posterior amygdaloid complex, with a comparison being made between the effects of the two test compounds.

A. Modifications Induced by the Test Compounds In the Electrocorticogram of Unanesthetized Test Animals Twenty-four hours prior to the test, the surface of a test animal's skull was exposed and stainless steel electrodes were screwed through the lamina externa to make contact with the dura matter in the frontal, parietal and occipital regions, on both sides of the median and transverse sutures. The ECoG was recorded on a REEGA MINI HUIT (Alvar Electronic) encephalograph with a transverse circuit, with bi-frontal, bi-parietal and bi-occipital leads and a longitudinal circuit, with fronto-parietal and parieto-occipital leads on both left and right. One track was used to record respiration, with leads from two steel needles placed under the shin, on either side of the thorax.

Some test animals were kept in restraint cases placed in a relatively soundproof room and some were left free to move in metal cases measuring 40×50×30 cm, which were also kept in a relatively quiet environment.

The activity of the test compounds studied was judged on the one hand by the pattern of spontaneous electrogenesis, especially by the relative degree to which the three basic rhythms of the ECoG in the animals were represented; the theta rhythm (4–8 c/sec.), predominant and characteristic of the state of wakefulness in the posterior regions; bursts of rapid spiked waves (alpha rhythm, 9–15 c/sec.) recorded in the course of diffused wakefulness, and slow waves (delta rhythm, 0.5–3 c/sec.) which are absent in a state of wakefulness except in pathological conditions or in the presence of medicinal substances, a rhythm characteristic of slow-wave sleep. The rapid, low-voltage beta rhythm, not very characteristic of the ECoG in the test animals used and primarily superimposed on the other rhythms, was not analyzed.

Possible modifications in cortical reactivity were also investigated, using two types of stimulation, one comprised an auditory stimulus (whistle blasts) and the other a nociceptive stimulus delivered to the cutaneous nerve endings by pinching the dorsal skin with Kocher's clamps.

To the foregoing qualitative analysis, a quantitative analysis concerning the evolution of spontaneous electrogenesis under the influence of test compounds 1 and 4 was added. The activity of the two compounds was judged by variations in an "R" index, defined as the ratio between the theta waking rhythm, slow waves and bursts of rapid spiked waves. Initially, R was evaluated quantitatively on a scale from 0 to 4 and after this initial estimate, variations in the R index were rated on a scale from 0 to 5 as follows:

1. Maintenance of the value calculated in making the reference tracking (basal value) 0 since variation is nil.
2. Reduction in basal values
   (a) reduction of basal value by one-half −1.
   (b) observed value between ½ and 1/5 of basal value −2.
   (c) observed value between 1/5 and 1/10 of basal value −3.
   (d) observed value between 1/10 and 1/20 of basal value −4.
   (e) observed value lower than 1/20 of basal value, reflecting maximum perturbation of spontaneous ECoG and expressing either a pathological condition or a state of slow-wave sleep, with the absence of theta rhythms and the exclusive presence of slow waves and/or bursts of rapid spiked waves −5.

Once the various values were allocated to each animal, the mean of these values were calculated for each experimental period. From these means, calculations were made of the percentages of variation as compared to a theoretical maximum value of −5 for each experimental period. The results are summarized in Table 13A1 below. The percentage for each period was calculated every 30 minutes for 7 hours, with a theoretical total of −10 per hour, then between 7 and 48 hours (theoretical total −15) and between the time of administering the test compound and the 48th hour (theoretical total −90). Variations of 10% were not regarded as significant. All dosages were administered intragastrically through the esophageal tube. The test compounds were suspended in a 1% aqueous CMC (carboxymethyl cellulose) solution, with a volume of 3 ml/kg per dose with the control animals receiving an equal volume of the solvent alone.

From the results obtained, and it will be appreciated that only summary results are included herein, it was determined that at doses of 7.5, 15 and 30 mg/kg the effects produced on spontaneous electrogenesis by compounds 1 and 4 were comparable in intensity and duration, the effects in both cases lasting at least 5 hours. After 6 hours, it was considered the the effects of the compounds had ceased since the percentage of variation had come down to about 10%, comparable to the effects observed in the control animals. Cortical reactivity induced by exteroceptive stimulation remained unchanged even in the presence of 30 mg/kg of either compound.

At lower doses, an effect lasting 2 hours with 1.5 mg/kg and an average of 4 hours with 3.75 mg/kg was noted, without being able to distinguish the activity of compound 1 from that of compound 4. The time lag before appearance of the effects of the two compounds was similar, 12 to 13 minutes, with extremes of 8 and 18 to 19 minutes. This latency seemed slightly prolonged, 21 minutes for compound 1 and 25 minutes for compound 4 with a dosage of 1.5 mg/kg.

TABLE 13A1

Absolute and Relative Variations in "R" Index: $R = \dfrac{\theta}{\alpha + \Delta}$

EXPERIMENTAL PERIODS

| Test Comp. | Dose in mg/kg | 1 Hour* Mean | % of Variation | 2 Hours* Mean | % of Variation | 3 Hours* Mean | % of Variation | 4 Hours* Mean | % of Variation |
|---|---|---|---|---|---|---|---|---|---|
| Controls | — | −0.5 | −5.0 | 0 | 0 | −1.0 | −10.0 | 0 | 0 |
| Test Compound #1 | 7.5 | −7.5 | −50.0 | −6.0 | −60.0 | −4.5 | −45.0 | −4.0 | −40.0 |
|  | 15.0 | −11.5 | −76.7 | −7.0 | −70.0 | −5.5 | −55.0 | −5.5 | −55.0 |
|  | 30.0 | −8.66 | −57.7 | −6.99 | −69.9 | −6.99 | −69.9 | −6.33 | −63.3 |
| Test Compound #4 | 7.5 | −9.5 | −63.3 | −7.5 | −75.0 | −6.0 | −60.0 | −3.0 | −30.0 |
|  | 15.0 | −13.0 | −86.7 | −8.5 | −85.0 | −7.0 | −70.0 | −5.5 | −55.0 |
|  | 30.0 | −6.99 | −46.7 | −5.32 | −53.2 | −6.32 | −63.2 | −4.99 | −49.9 |

|  | 5 Hours* Mean | % of Variation | 6 Hours* Mean | % of Variation | 7 Hours* Mean | % of Variation | 48 Hours** Mean | % of Variation | After 48 Hours*** Mean | % of Variation |
|---|---|---|---|---|---|---|---|---|---|---|
| Controls | −1.0 | −10.0 | −1.0 | −10.0 | −1.0 | −10.0 | 0 | 0 | −4.5 | −5.0 |
| Test Compound #1 | −3.0 | −30.0 | −2.0 | −20.0 | −1.5 | −15.0 | −0.5 | −3.3 | −29.0 | −32.2 |
|  | −4.0 | −40.0 | −2.0 | −20.0 | −2.0 | −20.0 | +1.5 | +10.0 | −36.0 | −40.0 |
|  | −4.33 | −43.3 | −1.32 | −13.2 | −0.99 | −9.9 | −1.66 | −11.1 | −37.3 | −41.4 |
| Test Compound #4 | −4.5 | −45.0 | −1.5 | −15.0 | −1.00 | −10.0 | 0 | 0 | −33.0 | −36.7 |
|  | −5.0 | −50.0 | −1.5 | −15.0 | −1.50 | −15.0 | +1.50 | +10.0 | −40.5 | −45.0 |
|  | −2.99 | −29.9 | −2.33 | −23.3 | −0.66 | −6.6 | −1.98 | −13.2 | −31.58 | −35.1 |

*Theoretical total = −10
**Theoretical total = −15
***Theoretical total = −90

Periods of intense arousal were also noted at a certain length of time after compound administration, with theta rhythms of 8 to 9 c/sec., which were difficult to characterize as "phases of physiological rebound", due to their short duration. It appeared possible, although not especially likely, that such phenomena were associated with phases of paradoxical sleep because bursts of ponto-geniculo-occipital waves were absent prior to such episodes. The ECoG Arousal phase results are summarized in Table 13A2 below.

In the group of animals receiving 30 mg/kg of the two test compounds, a respiratory depression was noted, starting at the same time as the first ECoG signs, reaching a maximum between 2 and 3 hours after administration, with a diminution in respiratory frequency at that time of 50% to 60%. This effect began to disappear at about 5 to 6 hours, but it was only after 24 hours that the depressive respiratory effect was completely extinguished.

The final observations were concerned with the influence of the test compounds on postural tonus. Evaluationg postural tonus in the animals kept in restraint cages was somewhat difficult. It was possible to judge this aspect by pulling the hind quarters of the animals out of the cage and observing whether the animals was capable of returning spontaneously to its position inside the cage, which control animals were able to do immediately. A slight reduction in the tonus of the animals treated with both compounds 1 and 4 was noted, with a slightly more pronounced effect in the presence of compound 4, especially at a dose level of 30 mg/kg. In one animal out of every three there was no attempt whatever, at 2½ hours, to resume the previous posture.

TABLE 13A2

| Test Compound | Dose in mg/kg | ECoG Arousal Phases Latency Period | Duration |
|---|---|---|---|
| Control | — | — | — |
| Test Compound #1 | 7.5 | 4 hrs. 50 mins. | 3 mins. |
|  | 15.0 | 2 hrs. 15 mins. | 4 mins. |
|  | 30.0 | 1 hr. 35 mins. | 3 mins. |

TABLE 13A2-continued

| Test Compound | Dose in mg/kg | ECoG Arousal Phases Latency Period | Duration |
|---|---|---|---|
| Test Compound #4 | 7.5 | 5 hrs. | 3 mins. 20 secs. |
|  | 30.0 | 4 hrs. 15 mins. | 2 mins. 40 secs. |

Generally speaking, the reduction in tonus appeared at some time between 30 and 120 minutes, with great individual variations.

In the test animals which were free to move, the first signs of sedation produced by the intragastric administration of 7.5 mg/kg of compounds 1 and 4 appeared, respectively, at 16 minutes (compound 1) and at 8 minutes (compound 4). Reflection by the ECoG of the activity of these test compounds was comparable to that already described relative to the animals under restraint. The duration of the effect was, however, shorter, not exceeding 3 hours under these conditions in contrast to the 5 hour minimum for restricted animals.

With the unrestricted animals, there was no loss of postural tonus, but only a slight ataxia. None of these test animals would submit at any time to a forced semi-lateral decubitus. Similarly, it was not possible to observe at any time during the 7 hours of recording any episodes of intense arousal comparable to those noted in the restrained animals.

A comparison of the effects produced by a 10 mg/kg dose of compound 3, administered under the same conditions to the unrestricted animals, with the effects of compounds 1 and 4, showed a great similarity, both in ECoG patterns produced by the three test compounds and in the duration of these effects, which lasted about 3½ hours.

B. Modifications Induced By Test Compounds 1 and 4 In The Electrogenesis Of Various Subcortical Centes This study was conducted with test animals weighing between 2.6 and 2.8 kg, following the stereotaxic method of Monnier and Gangloff (Atlas et techniques stereotaxique pour le cerveau du lopin eveille, 1961, Elsevier Pub. Co.), permitting the stimulation of certain subcortical structures as well as a simultaneous detection and recording of their electrical activities, which were compared to that of reference cortical electrodes. In this study, the subcortical centers considered were the caudate nucleus, the dorsal hippocampus, the lateral thalamus, the mesenephalic reticular formation, and the hypothalamic reticular formation. Test compounds 1 and 4 were administered by the intragastric route with an identical dose of 7.5 mg/kg.

Spontaneous activity in the subcortical centers of the unanesthetized animals is characterized by desynchronized activity consisting of high amplitude and relatively slow rhythms (4 to 5 c/sec.), alternating with low amplitude rapid rhythms (12 to 13 c/sec.). Tracings from the hippocampus and caudate nucleus sometimes takes the form of bursts, which is less commonly the case from the thalamus. These may occur at the same time as bursts of rapid spikes arising from the frontal cortex. During periods of arousal, this desynchronized activity is followed by a synchronized theta rhythm (7 to 8 c/sec.) from the hippocampus and caudate nucleus and from the median thalamus, whereas the cortical and reticular electrical activities are transformed into ultra-rapid and low voltage rhythms ($30\mu$ volts).

Cortical leads in animals receiving compounds 1 and 4 showed the same slowup of the basic rhythm and the periodic appearance of bursts of spikes was previously described. In addition, tracings of electrical activity from various subcortical centers disclosed a definite effect of compound 1 on the caudate nucleus as compared to that of compound 4. Under the effect of compound 1, bursts of rapid spikes appeared along with the cortical bursts and reached a maximum periodicity after 45 minutes. Although similar spikes were present, they were less distinguishable under the effect of compound 4.

Tracings from the rhinencephalon, especially the hippocampus, showed an increased amplitude, along with a general slowup of the basic rhythm. The theta rhythm characteristic of the activity on this structure took the form of sporadic bursts.

The thalamic rhythms were also perturbed, with greater amplitude and lower frequency in the presence of both compounds 1 and 4.

The electrical activity of the mesencephalic and hypothalamic reticular formations were also somewhat slower, especially in the presence of compound 4. The duration of this effect, limited to 45 to 60 minutes in the presence of compound 1, was prolonged to a minimum of 135 minutes in the presence of compound 4.

In a comparison with the activity of two well-known benzodiazepine derivatives, Valium (diazepam) and Librium (chlorodiazepoxide), there were no outstanding differences between these known derivatives and the activities of test compounds 1 and 4, except in tracings from the rhinencephalon. The EEG activity of the hippocampus, slow and of high amplitude under the effect of compounds 1 and 4, was depressed by Valium and Librium, with the theta rhythm appearing in the form of intermittent bursts. Bursts of rapid, spiked cortical and "caudate" waves appeared to be a consistent characteristic of the activity of this type of benzodiazepine derivatives. The role of the caudate nucleus in the regulation of extrapyramidal motor activity is well known and modifications of its EEG activity suggests a de-afferentation of this structure under the effects of these compounds, an effect related to the muscular relaxation and diminution of postural tonus (Cahn, J., Neuro-physical, Vol. 15, 1961, pages 134 et seq. and Cahn, J., et al; Neuro-psychopharmacology, Vol. 3, 1964, pages 490–493). In this connection, it is worthy of note that such periodic bursts appeared after about one hour in animals immobilized with Flaxedil (gallamine triethiodide).

Lastly, the more specific effect of compound 4 on the reticular EEG (especially the mesencephalic), suggests a sedative activity for this compound.

C. Modifications in the Threshold of Cortical and Hippocampal Alertness Produced by Stimulation of the Mesencephalic Reticular Formation (MRF) Median Thalamus and Posterior Hypothalamus In order to explain the selected test regions, a brief background discussion is presented. Repeated high frequency electric stimulation (200 c/sec.) of certain regions of the mesencephalan, from the bulb to the posterior hypothalamus, produces an arousal reaction in the cortex as well as a synchronization of subcortical rhythms. This portion of the mesencephalon constitutes the ascendant activating reticular system of the brain stem. It is also brought into play by sensory stimulation, through collateral nerves which depart from their specific pathways and act upon this structure, which is commonly designated as the mesencephalic reticular formation (MRF).

From the MRF, the extensions reach the cortex through two major pathways: one of these bypasses the thalamus and leads to the internal capsule; this constitutes the direct reticulo-cortical pathway and is responsible for diffuse, holocortical arousal: the other pathway passes through certain thalamic nuclei, the intralaminar nuclei constituting Jasper's diffuse thalamus; this pathway is responsible for a focalized arousal reaction which constitutes the "attention" phenomenon.

Direct high frequency electric stimulation of these non-specific nuclei gives rise to the same arousal reactions.

The common terminal extensions from the rhinencephalon proceed by the two major pathways, hypothalamic and epithalamic. The hypothalamic pathway is the principal one of the afferent pathways and has its origin in two bundles of fibers, from the olfactory and septal regions. When these fibers penetrate the preoptic area, they are joined by afferent branches from the amygdaloid complex, the hippocampus, Broca's great limbic lobe and the orbital cortex. The major group of fibers thus constituted is known as the median forebrain bundle and terminates in the reticular formation of the tegmentum mesencephali after receiving the anterior and posterior hypothalamo-tegmental bundles in the lateral hypothalamic region.

The posterior hypothalamo-tegmental bundle coming from the ventro-median nucleus of the hypothalamus and posterior hypothalamic regions is believed to include the fibers concerned in the control of emotional behavior. These formations as a whole belong to the circuit described by Papez, consisting among other elements of the posterior hypothalamus linked to the hippocampus through the fornix and the anterior nuclei of the thalamus through Vicq d'Azyr's bundle (fasciculus mamillothalamicus). Thus, after numerous relay points and complex detours, one arrives at the common affector pathway through which the rhinencephalon exerts its influence on the whole pattern of conduct of an individual. In the tegmen of the mesencephalon, fibers from the rhinencephalon connect with the ascendant and descendant pathways in this region, which is why the mesencephalon is such a vital crossroads in the central nervous system.

Intimately linked as it is with reticular activity, high frequency stimulation of the posterior hypothalamus induces cortical desynchronization, with disappearance of sleep spindles and a generalized subcortical arousal reaction.

Under emotional strain, messages originating in the rhinencephalan reach the peripheral affector nerves through the descending pathways. Increased activity in the hypothalamomesencephalic formation results in an augmentation of sympathetic discharge; which is related in particular to activation of the posterior hypothalamus.

Acted upon through the ascending pathways of mesencephalic origin and stimulated by impulses from varying sources, some bearing an emotional tinge, the whole neo-cortex, in turn controls the state of excitation of the underlying structures, thus attenuating effective reactions.

The test animals in this study were prepared by the techniques described by Monnier and Gangloff under the preceding study (infra B, page 30). Stimulation consisted of a series of waves delivered at a frequency of 200 c/sec., lasting 0.3 m sec., with a total duration of the stimulus being 5 sec. These shocks were delivered by a Neurovar neurostimulator (Alvar Electronic) coupled with a CRC cathode oscilloscope (type OC 343). Cerebral electrical activity was recorded on a REEGA MINI HUIT electroencephalograph (Alvar Electronic). The test animals were kept in restraint cages in a relatively soundproof room.

The activity of compounds 1 and 4 was tested in a series of six test animals for each compound, with a single dose of 7.5 mg/kg administered by the intragastric route. In each animal, the arousal threshold was determined for two of the three structures tested so that for each compound, each of the three structures stimulated were tested four times.

In making the baseline tracing, the threshold voltage was determined by a finding that the duration of the arousal reaction produced by the 5-second stimulation exceeded the duration of the stimulation by at least 5 seconds, that is, for a minimum of 10 seconds.

Under the influence of the compounds tested, the voltage was modified as required so as to obtain a period of arousal comparable to that of the baseline tracing, ±1 second.

The various thresholds were determined every 45 minutes after administration of the compounds, for a total period of four and one-half hours.

The critical value for raising of a threshold was fixed at 0.1 volts. This constituted the maximum variation recorded during 4½ hours in the control animals.

The results were taken in two forms and then summarized. In the first result, each animal was observed, yielding the values for the thresholds recorded at each time interval as well as the ratios of the values obtained in each of the stimulated structures. In the second result, again each animal was observed to attain the individual values of the arousal threshold and the relation between the structures stimulated, thus defining a preferential target point for each test compound in each of the afferent pathways to the hippocampus or the cortex. The summary (Table 13C hereinafter) shows for each of the stimulated structures, the mean percentage of variation in the cortical and hippocampal arousal thresholds as well as the average duration of the effects on these centers. The overall results of this study demonstrated that compound 1 preferentially reduces the excitability of the hypothalamo-cortical and hippocampal pathways, while the center least perturbed by compound 1 appears to be the MFR.

In contrast, compound 4 substantially raised the cortical and hippocampal arousal thresholds following stimulation of the reticular formation of the brain stem. On the other hand, the posterior hypothalamus appeared to be little affected by compound 4.

The arousal resulting from non-specific stimulation of the thalamus was moderately reduced in duration in a relatively similar manner by both compounds 1 and 4.

In light of the background given at the beginning of this study on the role of the various formations in the central nervous system, it appears that compound 1 acts as an anxiolytic substance, primarily through its preferential inhibitory impact on the structures controlling emotion (posterior hypothalamus) and compound 4 mainly acts as a sedative substance through the inhibitory effect it exerts on reticular excitability.

D. Modifications of After-Discharges Obtained Through Stimulation of the Dorsal Hippocampus and Posterior Amygdaloid Complex.

The rhinencephalon is a ring-like structure surrounding the hemispherical hilus, the limbic lobe (pars limbica rhinencephali-lobus limbicus), within which is the hippocampus or Ammon's Horn, supported in front and below by a veritable pedestal, consisting of the olfactory lobe or basal rhinencephalon (pars basalis rhinencephali-lobus olfactorius), containing the amygdaloid complex.

It is in these temporo-basal regions that one encounters the lowest convulsive thresholds, where the simplest form of irritation or the mere penetration of an electrode can trigger long-lasting paroxysinal discharges. This is especially true of the dorsal hippocampus and amygdaloid complex.

The hippocampal after-discharge, consisting of rhythmic spikes and abrupt discharges of multi-spike waves, is sometimes followed by a secondary discharge of very rapid spindles and is generally accompanied by a state of stupor. The amplitude of the spikes and waves is exceptional and may attain or even surpass 500 $\mu$volts, a fact which may explain the extension of the discharge to regions relatively distant from the point stimulated.

The amygdaloid after-discharge, obtained with slightly higher voltages, consists of a hyper-synchronized, high-amplitude discharge of 15 to 20 c/sec. This crisis spreads very slightly towards the other structures and often remains localized in the amygdaloid complex and hippocampus.

The test animals for this study were also prepared according to the technique described by Monnier and Gangloff (infra B, page 30) and the animals were kept in restraint cages in a relatively soundproof room.

The activity of test compounds 1 and 4 was assessed in identical groups of test animals for each compound, with identical numbers of animals for hippocampal after-discharges and for amygdaloid after-discharges. A dose of 7.5 mg/kg of each test compound was administered by the intragastric route. In each animal, after-discharges were triggered every 45 minutes after the administration of a test compound.

The stimulation consisted of a series of waves with a duration of 3 m sec., delivered at a frequency of 40 c/sec., with 5 seconds as the total duration of the stimulation. The shocks were delivered by a Neurovar neurostimulator (Alvar Electronic), coupled to a CRC cathode oscilloscope (type OC 343). Cerebral electric activity was recorded by REEGA MINI HUIT electroencephalograph (Alvar Electronic).

As can be seen from the results shown in Tables 13D1 and 13D2, compound 1 markedly increased the duration of after-discharges obtained by stimulation of the dorsal hippocampus at intervals between 45 minutes and 3 hours after administration. Beyond 3 hours, the duration of the after-discharge followed a pattern similar to that observed in the control animals. On the other hand, compound 4 had no apparent effect on the duration of the paroxysm.

Both compounds 1 and 4 exerted a lasting inhibitory effect on the after-discharge from the amygdaloid complex, this effect being slightly more pronounced in the presence of compound 1. In this connection, it is useful to note that the elaboration of emotional reactions by the rhinencephalon takes place at two levels of integration: the first of these is in the basal rhinencephalon, centered in the region of the amygdaloid complex, in liaison with the MFR and anterior hypothalamus; responses obtained from these regions are not completely developed and they are consequently elementary and are poorly adapted to given situation: the second level of integration is situated in the hippocampus and cingulate gyrus and gives rise to reactions which are appropriate to the situation.

Bearing these specialized functions in mind, the results of this study (Tables 13D1 and 13D2) tend to show that compound 1 passes anxiolytic properties, since it inhibits the activity of the amygdaloid complex, which represents a non-specific, stimulatory "reticular formation", while at the same time it reinforces the activity of the integrating hippocampal "cortex".

Compound 4 also reduces the excitability of the amygdaloid complex, but does not affect crises affecting the hippocampus. Accordingly, the potential anxiolytic effect of compound 4 appears less certain.

From the foregoing studies, one may conclude that a study of the spontaneous electrocorticogram in unanesthetized animals does not make it possible to differentiate the respective activities of compounds 1 and 4, either with regard to the type of modifications induced, which are typical of the benzodiazepines and analogous to those induced by Librium and Valium, or the intensity and duration of these modifications.

However, the study of subcortical electrical activity shows that both compounds 1 and 4 differ from other benzodiazepines which, like Valium and Librium, bring about a reduction in the amplitude of the hippocampal rhythm. Compounds 1 and 4, on the contrary, increase the amplitude of these activities and also reduce their frequency. The theta rhythm which is characteristic of this structure persists in the form of intermittent burst with both compounds.

The activities of compounds 1 and 4 contrast with one another in the different effects they have on the subcortical centers regulating basal vigilance and those controlling effective vigilance:

Compound 4 preferentially inhibits the excitability of the MFR.

Compound 1 has a particular effect on the posterior hypothalamus, reducing cortical and hippocampal arousal in response situations.

Compound 4 thus has more of the characteristics of a sedative since it affects basal vigilance without significantly modifying the after-discharge obtained by stimulating the rhinencephalon.

Compound 1, which exhibits a very samll sedative effect, acts primarily upon the complex of structures controlling the emotional sphere, the posterior hypothalamus, the hippocampus and the amygdaloid complex, and must therefore be regarded mainly as an anxiolytic agent.

TABLE 13C

Modifications of the Cortical and Hippocampal Arousal Thresholds

| Compound | Parameters | MRF Cortex | MRF Hippocampus | Median Thalamus Cortex | Median Thalamus Hippocampus | Posterior Hippocampus Cortex | Posterior Hippocampus Hippocampus |
|---|---|---|---|---|---|---|---|
| Test Compound 1 | % of Mean Variation | +57 | +50 | +67 | +73 | +83 | +78 |
| | Mean Duration | 1 hr. 10 mins. | 1 hr. 40 mins. | 3 hrs. 30 mins. | 2 hrs. 15 mins. | 3 hrs. 20 mins. | 2 hrs. |
| Test Compound 4 | % of Mean Variation | +311 | +308 | +67 | +67 | +56 | +60 |
| | Mean Duration | 2 hrs. 30 mins. | 2 hrs. 15 mins. | 3 hrs. | 3 hrs. | 1 hr. 40 mins. | 2 hrs. |

TABLE 13D1

Stimulation of the Limbic System - Duration in Seconds of Hippocampal After-Discharge

| Compound | Initial Score | 45 Mins. | 90 Mins. | 135 Mins. | 180 Mins. | 225 Mins. | 270 Mins. |
|---|---|---|---|---|---|---|---|
| Test Compound 1 Dose 7.5 mg/kg | 16. | 25 | 27 | 27 | 25 | 29 | 23 |
| | 13. | 14 | 21 | 16 | 23 | 26 | 26 |
| | 15. | 23 | 25 | 26 | 24 | 25 | 21 |
| | 14.5 | 18 | 11 | 19 | 24 | 23 | 23 |
| | 10. | 14 | 23 | 25 | 27 | 34 | 40 |
| Test Compound 4 | 10. | 10 | 7 | 6 | 8 | 9 | 10 |

TABLE 13D1-continued

| | Stimulation of the Limbic System - Duration in Seconds of Hippocampal After-Discharge | | | | | | |
|---|---|---|---|---|---|---|---|
| Compound | Initial Score | 45 Mins. | 90 Mins. | 135 Mins. | 180 Mins. | 225 Mins. | 270 Mins. |
| Dose 7.5 mg/kg | 15.5 | 20 | 16 | 15 | 10.5 | 19 | 22 |
| | 17.7 | 18 | 20 | 17.5 | 18 | 18.5 | 27 |
| | 12. | 14 | 15 | 13.5 | 18 | 13 | 13 |
| | 10. | 12 | 11 | 14 | 15 | 10 | 16 |

TABLE 13D2

| | Stimulation of the Limbic System - Duration in Seconds of Amygdaloid After-Discharge | | | | | | |
|---|---|---|---|---|---|---|---|
| Compound | Initial Score | 45 Mins. | 90 Mins. | 135 Mins. | 180 Mins. | 225 Mins. | 270 Mins. |
| Test Compound 1 | 40 | 15 | 17 | 46 | 17 | 42 | 45 |
| Dose 7.5 mg/kg | 26 | 0 | 0 | 0 | 0 | 46 | 62 |
| | 34 | 35 | 0 | 0 | 0 | 0 | 0 |
| | 24 | 22 | 27 | 37 | 34 | 35 | 30 |
| | 24 | 0 | 0 | 0 | 0 | 0 | 0 |
| Test Compound 4 | 42.5 | 29 | 32 | 35 | 33 | 37 | 38 |
| Dose 7.5 mg/kg | 59 | 43 | 46 | 27 | 33 | 37 | 42 |
| | 40 | 30 | 33 | 40 | 29 | 35 | 37 |
| | 42 | 35 | 40 | 40 | 33 | 34 | 39 |
| | 47.5 | 35 | 16 | 26 | 48 | 41 | 50 |

From the foregoing studies, a number of general conclusions may be drawn. The differences in pharmacological activity between compounds 1 and 4 are more pronounced than are their similarities, thus allowing one to distinguish between the probable therapeutic activities of these otherwise somewhat similar compounds.

While both compounds 1 and 4 potentiate the narcotic effect of a minimal dose of Veronal, only compound 4 brings about a degradation of motor coordination and, in proportion to the dose, reduces voluntary motility.

While both compounds 1 and 4 exert an anxiolytic effect in the four-plate study, the median anxiolytic dose ($AD_{50}$) of compound 1 is nearly three times less than that of compound 4. In other words, one may conclude that compound 1 produces an anxiolytic effect without prejudice to voluntary motility and coordination, whereas anxiolysis with compound 4 takes place only at dose levels which greatly depress muscular tonus.

The neurophysiological studies conducted, as a whole, confirm these different types of activities:

Compound 4 preferentially inhibits the excitability of the mesencephalic reticular formation, that is, it affects basal vigilance and possesses only a "sedative" effect, inasmuch as it has little influence or rhinencephalic after-discharge.

Compound 1, on the other hand, controls the emotional sphere, that is to say the posterior hypothalamus, the hippocampus and the amygdaloid complex so that it must be regarded primarily as an anxiolytic agent.

The invention is illustrated but not limited by the following Examples:

EXAMPLE 1

7-Chloro-2,3-dihydro-5-phenyl-1-propargyl-1H-1,4-benzodiazepin-2-one 3.76 g of 50% sodium hydride in mineral oil were added to 250 ml. of dimethylforamamide cooled to about 0° C. The temperature of the suspension was maintained at about 0° C., while a solution of 27.05 g (0.1 mol) of 7-chloro-2,3-dihydro-5-phenyl-1H-1,4-benzodiazepin-2-one in 50 ml. of dimethylformamide was added dropwise to it. The resulting mixture was stirred for 2 hours, and then 10 ml. of propargyl bromide were added dropwise while maintaining the temperature at 10°–15° C. The reaction mixture was stirred for about 4 hours and then poured over ice. The product was filtered and dissolved in chloroform; and the chloroform solution was separated from the aqueous layer, and dried over sodium sulphate. The chloroform was evaporated off from the solution and the residue was dissolved in the minimum quantity of a 7:3 (by volume) mixture of benzene and ethyl acetate. This solution was chromatographed on a column of silica gel and eluted with a 7:3 (by volume) mixture of benzene and ethyl acetate. The portion of eluate containing the desired product, as determined by thin-layer chromatography, was collected and evaporated under reduced pressure. The residue was recrystallized from a 1:1 (by volume) mixture of benzene and hexane, giving 16 g of the pure desired product with a melting point of 141°–143° C.

The hydrochloride and sulphate of the product had melting points, respectively, of 229°–231° C. and 166°–168° C. (with decomposition).

EXAMPLE 2

7-Chloro-2,3-dihydro-5-phenyl-1-propargyl-1H-1,4-benzodiazepin-2-one 100 ml. of a 1 N solution in sodium methoxide in methanol were added to a solution of 27.05 g (0.1 mol) of 7-chloro-2,3-dihydro-5-phenyl-1H-1,4-benzodiazepin-2-one in 500 ml. of anhydrous methanol. The solvent was driven off under reduced pressure, and the resulting sodium derivative was dissolved in 200 ml. of dimethylformamide. The temperature of the solution was maintained at 10°–15° C. while 10 ml. of propargyl bromide were added dropwise; and the mixture was stirred for about 4 hours, and then poured over ice. The product was filtered and dissolved in chloroform; and the chloroform solution was separated from the aqueous layer and dried over sodium sulphate. The chloroform was evaporated off from the solution, and the residue was dissolved in the minimum quantity of a 7:3 (by volume) mixture of benzene and ethyl acetate. This solution was chromatographed on a column of silica gel and eluted with a 7:3 (by volume) mixture of benzene and ethyl acetate. The portion of eluate containing the desired product, as determined by thin-layer chromatography, was collected and evaporated under reduced pressure. The residue was recrystallized from a 1:1 (by volume) mixture of benzene and hexane, giving 14 g of the pure desired product with a melting point of 141°–143° C.

We claim as our invention:

1. 7-Chloro-2,3-dihydro-5-phenyl-1-propargyl-1H-1,4-benzodiazepin-2-one and pharmaceutically acceptable acid addition salts thereof.

2. A pharmaceutical composition having high anxiolytic and relatively low myorelaxant properties comprised of an active compound selected from the group consisting of a pharmaceutically effective amount of 7-chloro-2,3-dihydro-5-phenyl-1-propargyl-1H-1,4-benzodiazepin-2-one and pharmaceutically acceptable acid addition salts thereof and a suitable pharmaceutical carrier.

* * * * *